United States Patent [19]
Hazlett et al.

[11] 3,985,876
[45] Oct. 12, 1976

[54] CHEMOTHERAPEUTIC SOLUTIONS CONTAINING A SULPHUR AND A SALT OF A 2,4-DIAMINO-5-BENZYLPYRIMIDINE

[75] Inventors: John R. Hazlett; Elvin A. Holstius, both of Greenville, N.C.

[73] Assignee: Burroughs Wellcome Co., Research Triangle Park, N.C.

[22] Filed: May 7, 1975

[21] Appl. No.: 575,142

Related U.S. Application Data

[63] Continuation of Ser. No. 428,917, Dec. 27, 1973, abandoned.

[30] Foreign Application Priority Data
Jan. 5, 1973  United Kingdom............ 690/73

[52] U.S. Cl............................ 424/229; 424/228
[51] Int. Cl.$^2$............... A61K 31/63; A61K 31/635

[58] Field of Search.................................. 424/229

[56] References Cited
UNITED STATES PATENTS

| 3,551,564 | 12/1970 | Klaui et al. .................. 424/229 |
| 3,728,452 | 4/1973 | Haber et al. .................. 424/229 |
| 3,881,003 | 4/1975 | Rehm.............................. 424/229 |

Primary Examiner—Sam Rosen
Attorney, Agent, or Firm—Donald Brown

[57] ABSTRACT

A clear solution suitable for oral or parenteral chemotherapy of microbial, especially bacterial, infections containing a sulfonamide in an organic solvent and a mono acid addition salt of a sulfonamide potentiator (e.g. trimethoprim) in water, the solution having a pH in the range 2 to 7.

14 Claims, No Drawings

CHEMOTHERAPEUTIC SOLUTIONS CONTAINING A SULPHUR AND A SALT OF A 2,4-DIAMINO-5-BENZYLPYRIMIDINE

This is a continuation of application Ser. No. 428,917, filed on Dec. 27, 1973 now abandoned.

The present invention relates to chemotherapeutic solutions containing a sulphonamide and a sulphonamide potentiator.

Aqueous injectable preparations containing both a sulphonamide and a sulphonamide potentiator have previously been prepared using a pharmaceutically acceptable salt of the sulphonamide, either with the sulphonamide potentiator in solution in a water miscible organic solvent or with the sulphonamide potentiator in the form of particles as a dispersion. In both of these cases the pH of the formulation is highly basic.

It has been found that when the pH range of the above solutions approach the lower end of the basic scale, i.e. approach neutral pH, insoluble complexes of the sulphonamide and the sulphonamide potentiator may form, e.g. insoluble complexes of sulfamethoxazole and trimethoprim. Formation of these complexes render the preparation unusable for injection purposes.

Although the above mentioned injectable preparations are useful they have certain limitations, i.e. their high pH may at times cause tissue damage at the injection site and at times haemolysis may occur and could cause formation of blood clots in the veins elsewhere. In addition, complexing may occur at a more rapid rate when the formulations are added to slightly acid or neutral intravenous solutions or drips, e.g. saline and dextrose.

It should be understood that the prior art dispersion is not suitable in any event for intravenous (hereinafter abbreviated to I.V.) use because of its particulate nature.

More particularly, common I.V. drips and infusions conventionally have a neutral to slightly acidic pH, e.g. saline, and accordingly if the injectable solution of the prior art is added to this type of infusion solution or drip, insoluble complexes tend to form prior to the complete infusion of the patient (conventionally it is desirable that patients be infused for periods of 8 to 24 hours).

It has also been found that the sterilization of basic pH injectable preparations utilizing an autoclave at 121° C for 20 minutes (a preferred sterilization technique because of its acceptability) usually causes the sulphonamide in the basic pH preparations, e.g. sulfamethoxazole, to oxidize and the preparation to take on a yellowish discoloration. This would make the injectable preparation unacceptable as a pharmaceutical product.

Accordingly, a new and improved injectable solution was required to overcome the limitations of the prior art injectable preparations. The invention described hereinafter overcomes the limitations of the above mentioned injectable preparations in that it is injectable directly into the veins (slowly) without causing clotting or tissue damage. In addition, the solution of this invention is compatible with acidic I.V. infusions such as saline, dextrose or Ringer's solution in that no precipitation occurs over long periods of time when used with solutions of sufficient volume. The product of this invention is also useful orally (undiluted or mixed with fluids), unlike highly basic solutions or preparations. Apart from pharmaceutical compatibility considerations, such highly basic solutions and preparations tend to cause tissue damage in the digestive system.

According to the present invention there is provided a clear solution for oral or parenteral administration, comprising a chemotherapeutic amount of sulphonamide having antimicrobial activity in a medicinally acceptable water - miscible organic solvent and an effective sulphonamide potentiating amount of a water - soluble, pharmaceutically acceptable mono acid addition salt of a sulphonamide potentiator in water, said clear solution having a pH in the range 2 to 7.

In a further aspect of the invention there is provided a method of making the above solution which comprises combining the sulphonamide, organic solvent, sulphonamide potentiator, in association with the appropriate amount of salt forming acid, and water and the adjusting, if necessary, the pH of the mixture so as to lie in the range 2 to 7 either by altering the proportions of the various components or by adding pharmaceutically acceptable acid.

In particular, this invention is directed to a new and improved clear aqueous injectable solution of a chemotherapeutic effective amount of a sulphonamide having antibacterial activity or other antimicrobial activity in a medicinally acceptable water miscible organic solvent and an effective sulphonamide potentiating amount of a water soluble pharmaceutically acceptable acid addition mono salt of a sulphonamide potentiator in water.

Additionally, it is preferable that the injectable solution contain an amount of a pharmaceutically acceptable acid sufficient to maintain the overall solution at a pH (acidic) to prevent the formation of an insoluble sulphonamide - sulphonamide potentiator complex after or during formation of the solution. The water soluble pharmaceutically acceptable salts of the sulphonamide-potentiator may be formed by the reaction of a sulphonamide-potentiator and a pharmaceutically acceptable acid.

A pharmaceutically acceptable mono acid addition salt of a sulphonamide potentiator or a mono acid addition salt of a pharmaceutically acceptable acid and a sulphonamide potentiator is defined herein as a salt consisting of a mono-protonated sulphonamide potentiator and an anion of a pharmaceutically acceptable acid. The pH of the solution and the Pka's of the pharmaceutically acceptable acid and the sulphonamide potentiator will determine their respective ionization status.

It is well known that the chemotherapeutic, especially the antibacterial, activities of the sulphonamides and of certain 2,4-diaminopyrimidines are mutually enhanced when these agents are acting together. Although the enhancement is mutual, these 2,4-diaminopyrimidines are herein referred to as sulphonamide potentiators.

Specific pyrimidines and methods of synthesis thereof are described; for example, in British Pat. Specifications Nos. 715, 815, 734, 801, 875, 562, 920, 412, 957, 797, 1,128,234, 1,133,766, 1,142,654, 1,223,881, 1,223,882, 1,261,455, 684,759, 774,094, 774,095, 913,710, 970,583, 1,084,103, 1,088,102, 1,129,084, U.S. Pat. Nos. 2,926,166 and 3,021,332, and South African Pat. No. 65/5618.

Sulphonamide potentiators of the foregoing classes are also disclosed in Belgian Pat. Nos. 782,153; 782,154; 774,281 and 789,904.

This invention is not limited to the use of a specific sulphonamide-potentiator. It is, however, important that the sulphonamide-potentiator form pharmaceutically acceptable mono acid addition salts which are soluble in water in satisfactory concentrations at physiologically acceptable pH levels.

An important class of such sulphonamide-potentiators particularly useful in this invention as pharmaceutically acceptable acid addition mono salts are 2,4-diaminopyrimidines carrying a substituted benzyl group in the 5-position together with or without a lower alkyl group in the 6-position.

More particularly preferred 2,4-diaminopyrimidines carrying a substituted benzyl group in the 5-position may be represented by the formula (I)

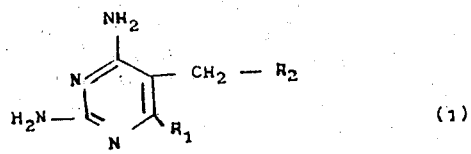

wherein $R_1$ is hydrogen or lower alkyl, e.g., methyl or ethyl, and $R_2$ is aryl; such as phenyl substituted by one or more alkoxy; such as lower alkoxy; such as, methoxy, ethoxy, or isobutox, amino, nitro, halogen, preferably chlorine, alkyl; such as lower alkyl; such as methyl, ethyl or trifluoromethyl, and hydroxy groups, particularly preferred is aryl of this formula II

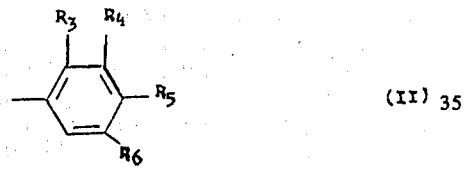

wherein one or both $R_3$ and $R_4$ are hydrogen, halogen, preferably chlorine, lower alkyl and lower alkoxy and wherein one or both $R_5$ and $R_6$ are halogen, preferably chlorine or bromine, lower alkyl and lower alkoxy.

In the above, alkyl and alkoxy are defined as containing 1 to 20 carbon atoms and lower alkyl and lower alkoxy are defined as containing from 1 to 6 carbon atoms and most preferably 1 to 3 carbon atoms and may contain straight or branched alkyl or alkoxy groups.

A class of 2,4-diamino-5benzylpyrimidines which are particularly preferred are those of formula:

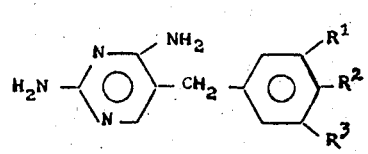

where $R^1$, $R^2$ and $R^3$ are the same or different and can each represent alkyl or alkoxy groups having from 1 to 4 carbon atoms, or $R^1$ and $R^2$ taken together can represent an alkylene dioxy group having from 1 to 4 carbon atoms such as a methylene dioxy group.

As specific compounds of high value there may be mentioned trimethoprim [2,4-diamino-5-(3,4,5-trimethoxybenzyl) pyrimidine], diaveridine [2,4-diamino-5-(3,4-dimethoxybenzyl) pyrimidine], 2,4-diamino-5-(3,4,6-trimethoxybenzyl) pyrimidine, ormetoprim [2,4-diamino-5-(2-methyl-4,5-dimethoxybenzyl)-pyrimidine], 2,4-diamino-5-(3,4-dimethoxy-5-bromobenzyl) pyrimidine, and pyrimethamine [2,4-diamino-5-(4-chlorophenyl)-6-ethylpyrimidine].

All these specific compounds are known to have highly valuable chemotherapeutic activity and to be potentiators of sulphonamides in the sense referred to above.

Substances which can be used as pharmaceutically acceptable acids to form water soluble pharmaceutically or medicinally acceptable mono salts of the sulphonamide potentiator, are—for example, pharmaceutically acceptable mineral acids such as sulfuric, phosphoric, hydrochloric, hydrobromic, hydroiodic, as well as pharmaceutically acceptable organic acids such as pharmaceutically acceptable carboxylic acids preferably having between 1 to 20 carbon atoms and most preferably 1 to 10 carbon atoms; e.g., tartaric, citric, lactic, embonic, salicyclic, glutamic, glutaric, naphthoic, acetic and ethylenediamine-tetra acetic acid and other pharmaceutically acceptable organic acids such as methane sulphonic acid. The acids used herein to form the salts or the salts of the sulphonamide potentiator must be stronger acids, i.e., have a lower pKa than the sulphonamide. At present, the preferred acid is citric acid, being conveniently accessible and acceptable for the practice of the invention.

This invention is not limited to the use of a specific sulphonamide. It is, however, important that the sulphonamide used be soluble in a medicinally acceptable organic solvent which is miscible in water and that the sulphonamide be sufficiently soluble in the organic solvent and the solutions of the invention at the desired concentrations. It is also important that the sulphonamide stay in solution in the organic solvent and the solutions of the invention at a physiologically acceptable pH value and not form a sulphonamide-sulphonamide potentiator insoluble complex.

Examples of sulphonamides having antimicrobial especially antibacterial activity and thus suitable for use in this invention are described in the text *Remington's Pharmaceutical Sciences*, Fourteenth Edition, Mack Publishing Company, Easton, Pennsylvania, copyrighted in 1970 by the Philadelphia College of Pharmacy and Science on pages 1195–1206 and are incorporated herein by reference hereto.

A convenient general formula for a preferred class of sulphonamides for use in the present invention is represented by formula III

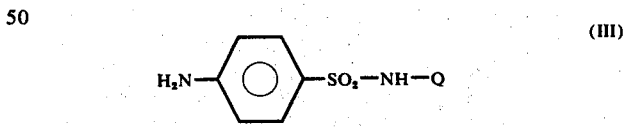

wherein Q is a substituted or unsubstituted pyrimidine-2-yl or -4-yl group or a substituted isoxazolyl group.

As examples of sulphonamides having antimicrobial e.g. antibacterial activity for use in this invention, the action of which is capable of being thus potentiated, there may be mentioned sulfadimethoxine [6-(4-aminobenzenesulphonamido)-2,4-dimethoxy-pyrimidine], sulphadiazine [2-(4-aminobenzenesulphonamideo) pyrimidine] sulfadoxine [4-(4-aminobenzenesulphonamido)-5,6-dimethoxypyrimidine], sulphadimethoxine [4-(4-aminobenzenesulphonamido)-2,6-dimethoxypyrimidine], sulphamethoxazol [3-(4-aminobenzenesulphonamido)-5-methylisoxazole], sulphaquinoxaline [2-sulphonamide-quinoxaline], sulphadimidine[2-(4-aminobenzenesulphonamido)-4,6-dimethylpyrimidine], sulfafurazole [5-(4-aminobenzenesulphonamido)-3,4-dimethylisoxazolo], and sulfacetamide[N-sulfanilyzacetamide].

The sulphonamides may be dissolved conveniently in a medicinally acceptable organic water miscible solvent preferably by stirring at room temperature. This may be accomplished readily either by adding the sulphonamide to the combination of the organic solvent and the water with or without the salt of the sulphonamide-potentiator present, or the sulphonamide may be mixed with the organic solvent and then both added to the water with or without the presence of the salt of the sulphonamide potentiator present. It is preferable to insure that the pH of the solution to which the sulphonamide or the salt of the sulphonamide potentiator is added in any order is maintained at a volume and pH sufficient to prevent formation of insoluble salts. In making the therapeutic solution of this invention the salt of the sulphonamide potentiator may be added for example, to the combination of the organic solvent, the water and the sulphonamide, or the salt of the sulphonamide potentiator may be formed by adding a pharmaceutically acceptable acid to the water with or without the presence of the organic solvent and with or without the presence of the sulphonamide by adding the sulphonamide-potentiator as base.

The end product formed, that is the solution of this invention, is precipitate free.

Suitable medicinally acceptable water miscible organic solvents for dissolving the sulphonamide include polar solvents such as N,N-dimethylacetamide, polyethylene glycols having average molecular weights from about 190 to 7500 and containing 2 to 159 ethylene glycol monomer ($CH_2CH_2O$) units, 1,2-propylene glycol, glycerin, hexamethylene glycol, 1,3-butylene glycol, ethanol, diethylacetamide, dimethylacetamide, dimethylsulfoxide, dimethylformamide, di 1,2-propylene glycol, glycerin formal, polyethylene-glycoethers of tetrahydrofurfuryl alcohol and diethylene glycol.

Usually the ratio of sulphonamide to sulphonamide potentiator as base useful to obtain a therapeutic effect is of the order of 5:1 (w/w), though ratios lying between 10:1 to 0.1:1 (w/w) are useful, and in certain cases it may be found desirable to have a ratio of as high as between 20:1 to 0.1:1 (w/w).

In accordance with this invention the injectable or oral solution contains from about 10 to 60 percent, preferably 15 to 50 percent and most preferably 20 to 40 percent (V/V) water and 30 to 90 percent, preferably 40 to 80 percent and most preferably 50 to 70 percent (V/V) of the organic solvent.

The injectable or oral solution also contains 1 to about 40 percent and preferably about 10 to 30 percent of the sulphonamide and from 1 to 10 percent and preferably 1 to 5 percent of the sulphonamide potentiator calculated as base. All percentages in this application mean W/V percentages unless other specified.

The pH of the solution of this invention is from 2 to 7 e.g., 2 to 6, preferably from 4 to 6 and most preferably from 4.5 to 5.5 especially for solutions of trimethoprim and sulfamethoxazole. The pH is preferably maintained within these pH limits by the addition of a sufficient amount of a pharmaceutically acceptable acid, the preferred amount being between 0.5 to 3.5%. Examples of suitable pharmaceutically acceptable acids as set forth earlier in the description are incorporated herein.

In order to add certain desirable properties to the injectable or oral solution product, it may be advantageous to add preservatives, local anaethesia components or other ingredients to enhance stability. Accordingly, it should be understood that other ingredients may be added so long as these additional ingredients do not detract from the desirable properties of the injectable or oral solution.

The quantity of the injectable or oral solution of this invention which can be injected into or oraly administered to a host mammal or animal for the treatment of bacterial infections or even protozoan infections (if the sulphonamide selected also possesses this activity) varies according to the species of the host, its size, its are, general condition of health and severity and type of infection. Conveniently from about 1 ml. to about 1000 ml. of a solution containing about 5 percent W./V. of the sulphonamide potentiator and about 25 percent W./V. of the sulphonamide can be employed in the treatment of bacterial infections such as those caused by proteus or mirabelis hemophilus influenza.

The frequency at which the injectable or oral solution of this invention will be administered to a host will vary depending upon the quantity of the active medicaments present therein and the needs and requirements of the host.

Under ordinary circumstances, however, up to about 200 mg/kg of the sulphonamide and up to about 150 mg/kg of the sulphonamide potentiator (calculated as base) in combinations can be administered daily in several dosages. It is to be understood, however, that the mentioned ranges are in no sense critical and the dosages can be adjusted in accordance with the needs of the host.

The product of this invention is primarily intended for parenteral use. However, it can be used orally undiluted or for example, with the addition thereof to drinking water, milk, fruit juices, etc.

Flavourings such as cherry, orange, etc. may be added.

Oral solutions of this inventions are particularly convenient for the treatment of humans, most particularly children, and in poultry for the treatment of coccidiosis.

The following examples further illustrate this invention. It is to be noted that all temperatures are in degrees centigrade, unless otherwise specified and where no temperature is given for the mixing of the ingredients or to prepare the salt, room temperature is the temperature at which the ingredients were mixed or at which temperature the salt was formed. Obviously higher or lower temperatures may be used depending on how quickly it is desired for the mixing or the formation of the salt to take place as is well known by those skilled in the art. All percentages in this application mean W/V percentages, unless otherwise specified.

EXAMPLE 1

The following ingredients were used:

| | |
|---|---|
| Citric Acid (anhydrous) | 1.2 g. |
| Sulfamethoxazole (SMX) | 8.0 g. |
| Trimethoprim (TMP) | 1.6 g. |
| Polyethylene Glycol 400 | 30.0 ml. |
| Propylene Glycol | 40.0 ml. |
| USP Alcohol (95% ethanol) | 13.0 ml |

-continued

| | |
|---|---|
| Water | 17.0 ml. |

The citric acid was dissolved in the water. The USP alcohol and propylene glycol were added with stirring to the water. With continuous stirring, the TMP was added to the above. The Polyethylene Glycol 400 and SMX were added and the mixture stirred until clear. The pH was 4.6. The solution was vacuum filtered through Whatman No. 2 filter paper. The solution was sparged with nitrogen for 30 seconds and filled into 5 ml. ampuls. The area above the solution was purged with nitrogen for 10 seconds. The ampuls were heat sealed and autoclaved at 121° C. for 20 minutes.

EXAMPLE 2

Example 1 was repeated except that 0.1 g. of potassium metabisulfite was added to the water after the citric acid. Also, nitrogen was not used. The solution was autoclaved at 121° C. for 20 minutes.

EXAMPLE 3

The following ingredients were used:

| | |
|---|---|
| Citric Acid (anhydrous) | 1.2 g. |
| Sulfamethoxazole | 8.0 g. |
| Trimethoprim | 1.6 g. |
| N,N-Dimethylacetamide (DMA) | 50.0 ml. |
| Water | 50.0 ml. |

The citric acid was dissolved in the water. The TMP was added to the solution and stirred until clear. The DMA and SMX were added and the mixture stirred until clear. The pH of the solution was 4.6. The solution was vacuum filtered through Whatman No. 2 filter paper. The solution was sparged with nitrogen for 30 minutes and filled in 5 ml. ampuls. The area above the solution was purged with nitrogen for 10 seconds. The ampuls were heat sealed and autoclaved at 121° C. for 20 minutes.

EXAMPLE 4

Example 3 was repeated except that 0.6 g. of citric acid was used giving a solution with pH 5.6.

EXAMPLE 5

The contents of one ampul (5 ml.) of the product of Example 3 were drawn into a syringe and injected into 1 liter of 0.9% sodium chloride with agitation. No precipitate appeared within 16 hours.

EXAMPLE 6

The procedure used in Example 5 was followed except a solution of 8.60 g. sodium chloride and 0.33 g. calcium chloride with sufficient water to make 1 liter, commonly referred to as Ringers Solution, was used instead of 0.9% sodium chloride. No precipitate was observed within 16 hours.

EXAMPLE 7

The following ingredients were used:

| | |
|---|---|
| Citric Acid (anhydrous) | 1.0 g. |
| Polyethylene Glycol 400 | 50.0 ml. |
| USP Alcohol (95% ethanol) | 10.0 ml. |
| Propylene Glycol | 10.0 ml. |
| Sulfamethoxazole | 8.0 g. |
| Trimethoprim | 1.6 g. |
| Water | 30.0 ml. |

The citric acid was dissolved in the water. The TMP was then added with continuous stirring until solution was affected. The Polyethylene Glycol 400, USP alcohol (95% ethanol), propylene glycol, and SMX were added to the above and the mixture stirred til the solids dissolved. The pH was 4.6. The solution was vacuum filtered through Whatman No. 2 filter paper. The solution was nitrogen sparged, filled into 5 ml. ampuls, nitrogen purged, heat sealed, and autoclaved at 121° C. for 20 minutes.

In Examples 9 and 10 following the method of Example 1, the listed ingredients were mixed and 8 g. of sulfamethoxazole and 1.6 g. of trimethoprim were dissolved therein. In Examples 11 and 12 following the method of Example 3, the listed ingredients were mixed and 8 g. of sulfamethoxazole and 1.6 g. of trimethoprim were dissolved therein. In Examples 13 and 14 following the method of Example 8, the listed ingredients were mixed and 8 g. of sulfamethoxazole and 1.6 g. of trimethoprim were dissolved therein.

| mole | Water | Citric Acid (anhydrous) | Polyethylene Glycol** | N,N-dimethylacetamide | USP Alcohol | Propylene Glycol | pH | Notes |
|---|---|---|---|---|---|---|---|---|
| 9 | 15 | 1.2 | 400/30 | — | 10 | 45 | 4.7 | |
| 10 | 40 | 1.2 | 400/50 | — | 10 | — | 4.9 | |
| 11 | 50 | 1.2 | 400/10 | 40 | — | — | 4.6 | |
| 12 | 50 | 0.9 | 6000***/12 | 40 | — | — | 4.6 | |
| 13 | 50 | 0.9 | 400/10 | 38 | — | — | 4.6 | 2 ml. Benzyl Alcohol was also added |
| 14 | 50 | 0.9 | 4000***/24 | 30 | — | — | 5.0 | |

*Liquids are by volume in ml., solids by weight in grams
**The first number indicates the polyethylene glycol used, the second the volume in ml. (or the weight in grams for example, 13 and 14)
***Solids

EXAMPLE 15

The following ingredients were used:

| | |
|---|---|
| DMA | 7.5 ml. |
| Sulfacetamide | 2.0 g. |
| Citric Acid (ahydrous) | 0.15 g. |
| Trimethoprim | 0.40 g. |
| Water | 17.5 m. |

The citric acid was dissolved in the water. The TMP was added and the mixture was stirred until a clear solution was obtained. The DMA and sulfacetamide were added and the mixture stirred til clear. The pH of the solution was 4.7.

EXAMPLE 16

The following ingredients were used:

| | |
|---|---|
| Sulfamethoxazole | 2.0 g. |
| Trimethoprim | 0.4 g. |
| Water | 12.5 ml. |
| DMA | 12.5 ml. |
| Glacial Acetic Acid | 0.1 ml. |

The glacial acetic acid and DMA were added to the water and mixed. The TMP was added and the mixture stirred until clear. The SMX was added and the mixture stirred to give a clear solution. The pH of the solution was 5.8.

EXAMPLE 17

The following ingredients were used:

| | | |
|---|---|---|
| Water | 15.0 | ml. |
| Citric Acid (anhydrous) | 0.03 | grams |
| Trimethoprim | 0.03 | grams |
| Polyethylene Glycol 1000 | 7.5 | grams |
| Sulfamethoxazole | 0.125 | grams |

The citric Acid was dissolved in water. The trimethoprim was added and the mixture stirred until clear. The polyethylene glycol and the sulfamethoxazole were added and the mixture stirred until clear. The pH of the injectable solution was 4.0.

EXAMPLES 18 – 21

Example 1 was repeated with the exception that instead of trimethoprim there was used as the sulfonamide potentiator the following pyrimidines: 2,4-diamino-5-(3,4-methylenedioxy-5-methoxybenzyl)-pyrimidine; 2,4-diamino-5-(3,5-diethyl-4-methoxybenzyl)pyrimidine; 2,4-diamino-5-(3,5-dimethoxy 4-methylbenzyl)pyrimidine and 2,4-diamino-5-(3,4,5-triethylbenzyl)pyrimidine.

ORAL TRIMETHOPRIM/SULFAMETHOXAZOLE FORMULATION EXAMPLES

EXAMPLE 22

The following ingredients were used:

| | |
|---|---|
| USP Alcohol (95% Ethanol) | 9.0 ml. |
| Citric Acid, anhydrous | 0.9 g. |
| Liquid Sucrose | 10.0 ml. |
| Polyethylene Glycol 400 | 46.0 ml. |
| Potassium metabisulfite | 0.1 g. |
| Sodium Saccharin | 0.1 g. |
| Sulfamethoxazole | 8.0 g. |
| Trimethoprim | 1.0 g. |
| Flavor, soluble | q.s. |
| Water, purified, q.s. to | 100.0 ml. |

The citric acid, sodium saccharin and potassium metabisulfite were dissolved in water. The polyethylene glycol 400 was then dissolved in the solution, and the liquid sucrose, alcohol, and soluble flavor were added with stirring. The trimethoprim was added and stirring was continued until the trimethoprim dissolved. The sulfamethoxazole was added, and the mixture was stirred until a clear solution suitable for oral administration was obtained. Suitable soluble flavoring agents may be either natural flavors, e.g. lime, orange, or artificial flavors, e.g. cherry, raspberry.

EXAMPLES 23 and 24

Following the general procedure of Example 22 solutions useful for oral administration were prepared containing the following ingredients:

| | Example 23 | Example 24 |
|---|---|---|
| USP Alcohol (95% Ethanol) | — | 5.0 ml. |
| Citric Acid, anhydrous | 0.9 g. | 0.9 g. |
| Flavor, soluble | q.s. | q.s. |
| Glycerin | — | 10.0 ml. |
| Liquid Sucrose | 10.0 ml. | 10.0 ml. |
| Polyethylene Glycol 4000 | 60.0 ml. | 48.0 ml. |
| Sulfamethoxazole | 8.0 g. | 8.0 g. |
| Trimethoprim | 1.6 g. | 1.6 g. |
| Water, purified | 30.0 ml. | 35.0 ml. |

We claim:
1. A clear solution which includes 1 to 40 per cent (w/v) of sulfamethoxazole, 1 to 10 percent (w/v) of trimethoprim calculated as base in the form of a water soluble pharmaceutically acceptable acid addition mono salt, 10 to 60 percent water (v/v) and 30 to 90 percent (v/v) of a water miscible organic solvent for the sulfamethoxazole, the solution having a pH of 4.0 to 7.0, and a solution in which the organic solvent is selected from the class consisting of N, N-dimethylacetamide, polyethylene glycols having average molecular weights from about 190 to 7500 and containing 2 to 159 ethylene glycol monomer units, 1, 2-propylene glycol, glycerin, hexamethylene glycol, 1,3-butylene glycol, ethanol, diethylacetamide, dimethylsulfoxide, dimethylformamide, di 1,2-propylene glycol, glycerin formal, polyethylene-glycoethers of tetrahydrofurfuryl alcohol and diethylene glycol.

2. A solution according to claim 1 in which the salt is the lactate salt.

3. A solution according to claim 1 wherein the ratio of sulfamethoxazole to trimethoprim as base is 20:1 to 0.1:1.

4. A solution according to claim 3 in which the solution contains from 0.5 to 3.5 percent of a pharmaceutically acceptable acid.

5. The solution of claim 1 which has a pH between 4 to 6.

6. The solution of claim 1 which has a pH of 4.5 to 5.5.

7. A clear solution for oral or parenteral use including (a) 1 to 40 per cent (w/v) of a sulphonamide selected from the group consisting of sulfadimethoxine, sulphadiazine, sulfadoxine, sulphadimethoxine, sulphamethoxazol, sulphaquinoxaline, sulphadimidine, sulfafurazole and sulfacetamide; (b) 30 to 90 percent (v/v) of a medicinally acceptable water miscible organic solvent for the sulphonamide, said organic solvent is selected from the class consisting of N,N-dimethylacetamide, polyethylene glycols having average molecular weights from about 190 to 7500 and containing 2 to 159 ethylene glycol monomer units, 1,2-propylene glycol, glycerin, hexamethylene glycol, 1,3-butylene glycol, ethanol, diethylacetamide, dimethylsulfoxide, dimethylformamide, di 1,2-propylene glycol, glycerin formal, polyethylene-glycoethers of tetrahydrofurfuryl alcohol and diethylene glycol; (c) 1 to 10 percent (w/v) of sulphonamide potentiator calculated as a base, in the form of a water soluble, pharmaceutically acceptable mono acid addition salt, said sulphonamide potentiator being of formula I

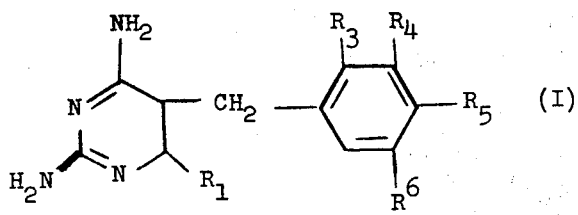

wherein $R_1$ is hydrogen or lower alkyl, wherein $R_3$ and $R_4$ are hydrogen, halogen, lower alkyl, lower alkoxy and wherein one or both $R_5$ and $R_6$ are halogen, lower alkyl and lower alkoxy; and (d) 10 to 60 percent water (v/v) said solution having a pH in the range of 2 to 7.

8. A solution as claimed in claim 7 wherein $R_3$ is hydrogen, and $R_4$, $R_5$ and $R_6$ are the same or different and represent an alkyl or alkoxy group having from 1 to 4 carbon atoms.

9. A solution according to claim 7 in which the sulphonamide potentiator is represented by the formula:

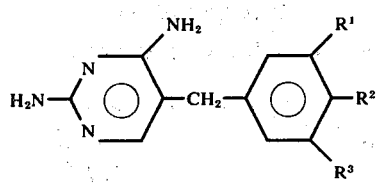

where $R^1$, $R^2$ and $R^3$ are the same or different and can each represent alkyl or alkoxy groups having from 1 to 4 carbon atoms.

10. A solution according to claim 9 in which $R_1$, $R_2$, and $R_3$ are methoxy.

11. A solution according to claim 9 wherein the sulphonamide is sulfamethoxazole.

12. A solution according to claim 7 in which the sulphonamide is present in an effective antibacterial or antiprotozoal treatment amount and in which the sulphonamide potentiator is present in an effective sulphonamide potentiating amount.

13. A method of treating an animal or mammal suffering from bacterial or protazoal infections which comprises administering to said animal or mammal a therapeutically effective antibacterial or antiprotozoal treatment amount of the solution of claim 7.

14. A method according to claim 13 in which the sulphonamide is sulfamethoxazole and the potentiator is trimethoprim.

* * * * *

Disclaimer 3,985,876.—*John R. Hazlett* and *Elvin A. Holstius*, Greenville, N. C. CHEMOTHERAPEUTIC SOLUTIONS CONTAINING A SULPHUR AND A SALT OF A 2,4-DIAMINO-5-BENZYLPYRIMIDINE. Patent dated Oct. 12, 1976. Disclaimer filed May 10, 1977, by the assignee, *Burroughs Wellcome Co.*

Hereby enters this disclaimer to claims 1 to 14 of said patent.

[*Official Gazette July 26, 1977.*]